(12) United States Patent
Emmenegger et al.

(10) Patent No.: US 8,030,287 B2
(45) Date of Patent: Oct. 4, 2011

(54) DNA VACCINE AGAINST NORTH AMERICAN SPRING VIREMIA OF CARP VIRUS

(75) Inventors: Eveline J. Emmenegger, Seattle, WA (US); Gael Kurath, Seattle, WA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 214 days.

(21) Appl. No.: 12/148,210

(22) Filed: Apr. 17, 2008

(65) Prior Publication Data

US 2009/0196881 A1 Aug. 6, 2009

Related U.S. Application Data

(60) Provisional application No. 60/959,928, filed on Jun. 26, 2007.

(51) Int. Cl.
*A61K 48/00* (2006.01)
*A61K 45/00* (2006.01)
*C07H 21/02* (2006.01)

(52) U.S. Cl. .................. 514/44 R; 424/278.1; 536/23.1

(58) Field of Classification Search ................ 514/44 R
See application file for complete search history.

(56) References Cited

OTHER PUBLICATIONS

Kanellos, 2006, Vaccine, 24:4927-4933.*
Cranenburgh, 2001, Nucl Acid Res, 29:e26, 1-6.*

* cited by examiner

*Primary Examiner* — Valerie Bertoglio
(74) *Attorney, Agent, or Firm* — Elizabeth Arwine

(57) ABSTRACT

In this application is described a novel DNA vaccine for Spring viremia of carp virus. The candidate vaccine a SVCV glycoprotein (G) gene from the North Carolina isolate. The DNA vaccine provides protection in vaccinated fish against challenge with the SVCV.

22 Claims, 4 Drawing Sheets

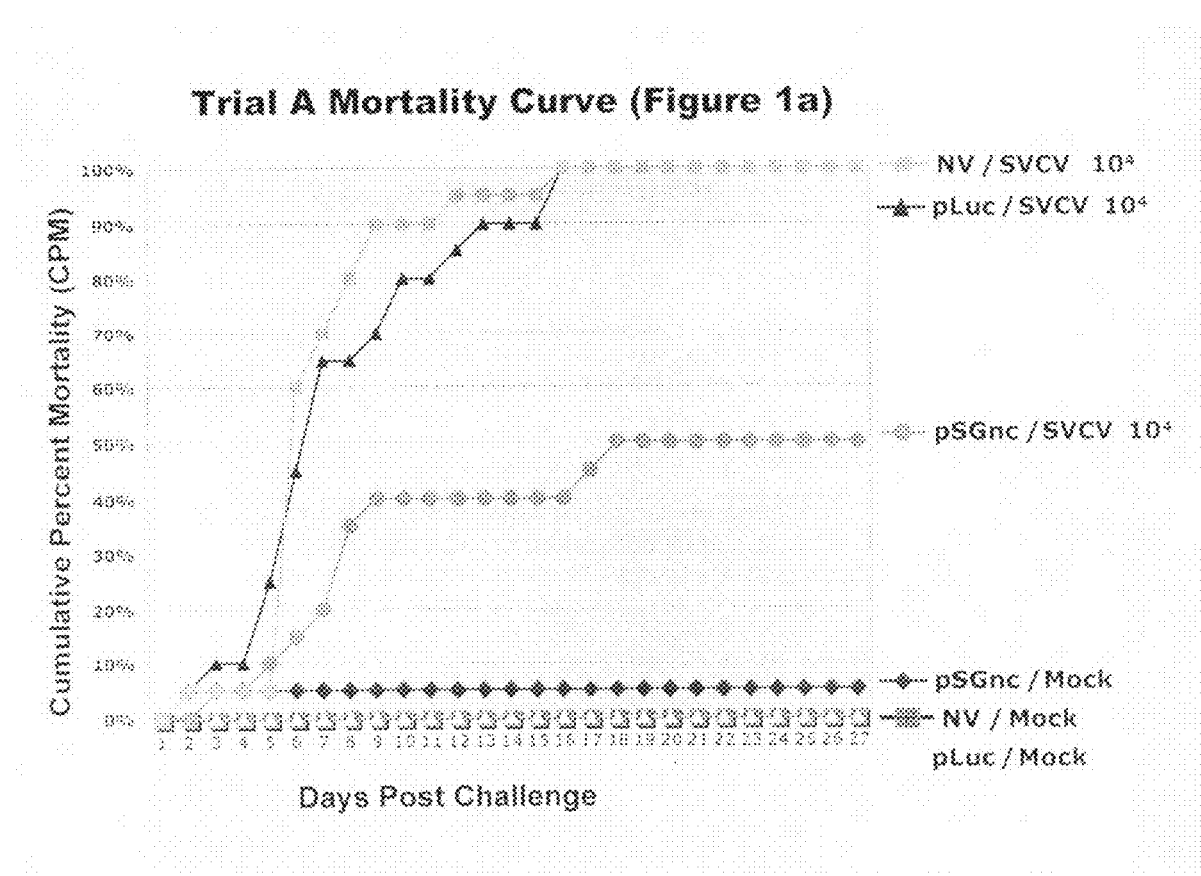

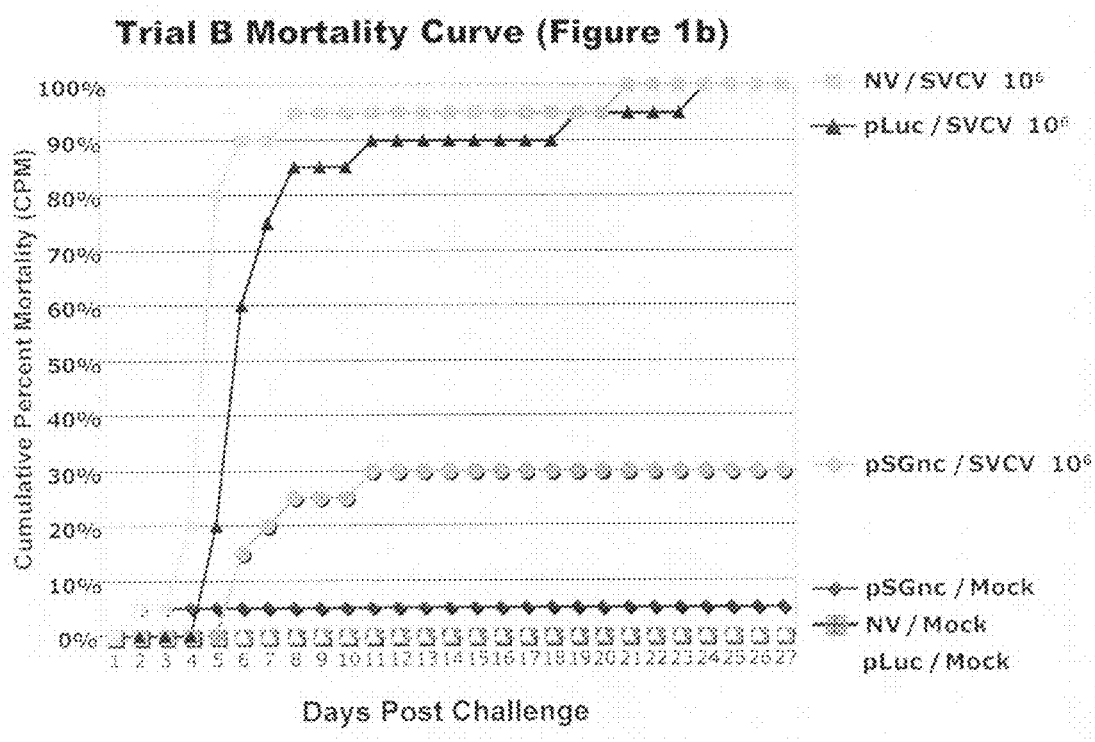

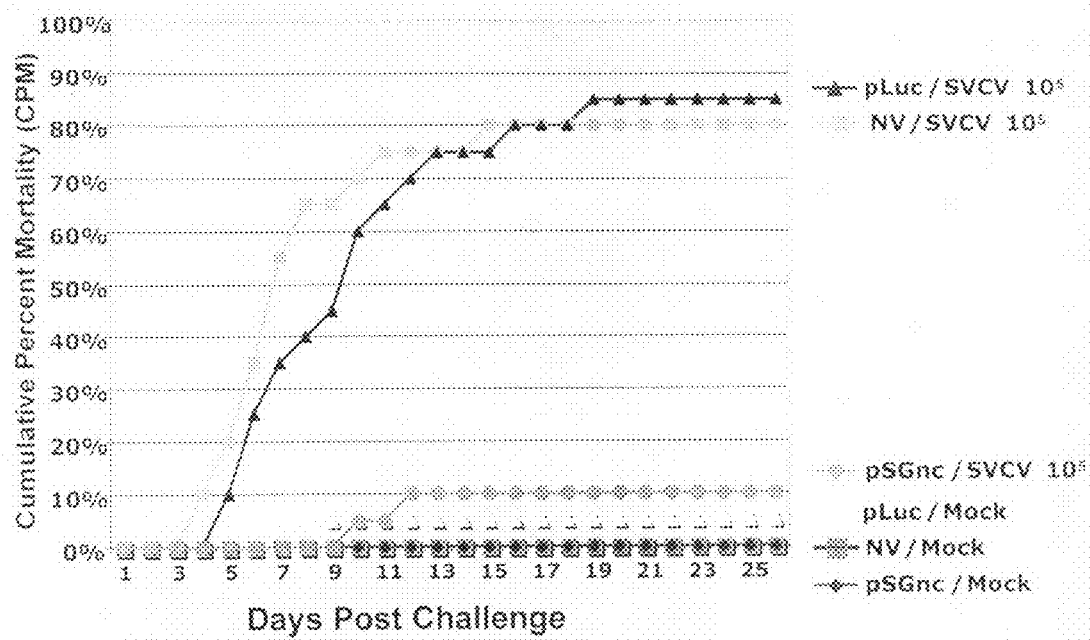

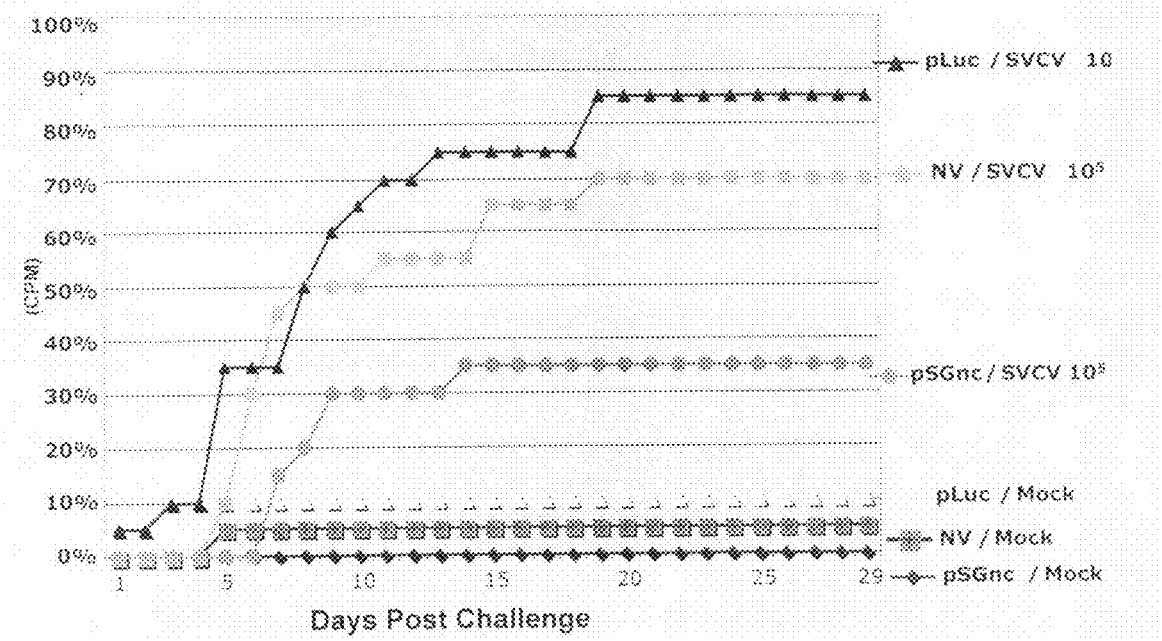

DNA VACCINE AGAINST NORTH AMERICAN SPRING VIREMIA OF CARP VIRUS

This application claims the benefit of priority from Provisional Application Ser. No. 60/959,928 filed on Jun. 26, 2007.

INTRODUCTION

Spring viremia of carp virus (SVCV) is a rhabdoviral pathogen that has frequently decimated common carp (*Cyprinus carpio carpio*) stocks throughout Europe since its first description in the 1970s (Fijan et al. 1971, Veterinary Archives 41, 125-138; Ahne et al. 2002, Diseases of Aquatic Organisms 52, 261-272). Currently in Europe, carp populations from the countries of Russia, Romania, Netherlands, Moldavia, Georgia, Germany, France, United Kingdom, and Denmark have the highest reported prevalence (Dixon 2005, Impacts, control and regulation of SVCV in wild and cultured fish in western Europe with a history of SVCV strains from China. 30$^{th}$ Eastern Fish Health Workshop, Spring Viremia of Carp Virus Continuing Education Course). In fish species that succumb to infection by SVCV, the spleen, kidney, intestines, and air bladder are typically inflamed, hemorrhaging, or swollen. Disease progression leads to necrosis of the internal organs and eventually death. Outbreaks at common carp farms in Europe normally occur in the spring, as the water temperature begins to rise after a cold winter period. The highest fish mortalities due to SVCV infection occur between 11° C. and 17° C. (Ahne 1986, Veterinary Immunology and Immunopathology 12: 383-386; Fijan 1988, Vaccination against spring viraemia of carp. In: Fish Vaccination, ed. A. E. Ellis, London: Academic Press, p. 204-215). Common carp belonging to the Cyprinidae family are the principal host species of SVCV (Fijan 1999, Spring viremia of carp and other viral diseases of warm-water fish. In Woo PTK, Bruno D W (eds) Fish diseases and disorders, Vol. 3. CAB International, Oxon, p. 177-244). Natural infections of SVCV have also occurred in other cyprinid fish including koi (*Cyprinus carpio* koi), goldfish (*Carassius auratus*), crucian carp (*Carassius carassius*), silver carp (*Hypopthalmichthys molitirix*), bighead carp (*Aristichthys nobilis*), grass carp (*Ctenopharyngodon idella*), orfe (*Leucisucus idus*), and tench (*Tinca tinca*) (Fijan 1999, supra; OIE 2006, Office International des Epizooties, Manual of diagnostic for Aquatic Animals, Spring Viremia of Carp, Chapter 2.1.4). The experimental infection of other cyprinids, such as roach (*Rutilus rutilius*), zebrafish (*Danio rerio*), and fathead minnow (*Pimephales promelas*) suggests that cyprinids may be inherently susceptible to SVCV and when stressed succumb to infection (Haenen and Davidse 1983, Diseases of Aquatic Organisms 15, 87-92; Sanders et al. 2003 Comp. Med. 53, 514-521). Fish species from the families of Poeciliidae, Esocidae, Centrarchidae, Siluridae, and Salmonidae have also been infected by SVCV (Svetlana et al. 2006, Acta Veterinaria 56, 553-558; Ahne et al. 2002, supra). Due to the highly infectious nature of SVCV and potential impact this virus could have on susceptible fish populations globally, any detection of SVCV requires notification within 48 hours to the Office of Internationale Epizootic (OIE), the organization charged with regulating world animal health. SVCV is one of only nine piscine viruses recognized worldwide by the OIE as a notifiable animal disease.

In April of 2002 at one of the largest koi production facilities in the United States yearling koi from one pond began dying from SVCV (Goodwin 2002, J. Aquatic Animal Health 14, 161-164). Subsequently the virus was detected in other ponds at the facility, fifteen thousand fish died from SVCV and another 135,000 fish were euthanized from ponds located both in North Carolina and Virginia (USDA APHIS 2002). One month later in an apparently unrelated incident, dead wild carp began washing up on the shores of a Wisconsin lake. Mortalities reached 1,500 and the causative agent of the epidemic was SVCV (Dikkeboom et al. 2004, J. Aquatic Animal Health 16, 169-178). One year later the virus was isolated from a healthy common carp during a fish health screening in an Illinois water channel that is linked to Lake Michigan. In 2004 there were two outbreaks of SVCV, one at a private koi pond in Washington State and the other at a commercial koi hatchery in Missouri (Warg et al. 2007, Virus Genes 35, 87-95). Recently in June 2006, SVCV was found for the first time in Canada in common carp from Lake Ontario (Garver et al. 2007, J. Fish Diseases 30, 665-671). These fish were scheduled for shipment to France, but the virus was detected during an exportation disease screening. Later in October 2006 the United States Department of Agriculture (USDA) instituted regulations restricting the importation of live fish, fertilized eggs, and gametes of specific fish species susceptible to SVCV. Until the first outbreak in 2002, SVCV had never been reported in North America. Six isolations of this exotic virus in the past five years and the import restrictions placed on SVCV susceptible fish are warnings of the potential invasiveness and impact SVCV could have on vulnerable fish stocks in North America.

Eradication of SVCV infected fish and hygiene measures are the standard methods used to combat SVCV (Fijan 1984a, Symposia Biologica Hungrica 23, 17-24; Wolf 1988, Infectious hematopoietic necrosis virus, In Fish viruses and fish viral diseases. Cornell University Press: Ithaca, N.Y., p. 191-211; Ahne et al. 2002, supra). Therapeutic and preventative strategies to control SVCV have been ineffective and as such there is no commercially available SVCV vaccine. There have been previous reports of inactivated SVCV vaccines using European strains providing limited protection (Tesarcik and Macura 1981, Bulletin VURH Vonany 17, 3-11; Tesarcik and Macura 1988, Spring viremia of carp—development of a vaccine in Czechoslovakia. In: Ichtyopathology in Aquaculture, eds. N. Fijan, S. Cvetnic, and T. Wikerhauser, JAZU, Zagreb; Tesarckik et al. 1978, Bulletin VURH Vodnany 14, 3-6; Macura et al. 1983, Pr. VURH Vodnany 12, 50-56; Tesarcik et al. 1984, Pr. VURH Vodnany 13, 68-74). However, continued research on the inactivated SVCV vaccine has not been pursued in part due to the risks associated with incomplete activation of the virus, cumbersome legal and marketing restrictions, prohibitively expensive production, and the lack of a quantitative assessment of the protection levels provided by the vaccine (Fijan 1984b, Symposium Biol. Hungay 23, 233-241; Wolf 1988, supra).

DNA vaccines targeted against viral pathogens are an attractive alternative to traditional vaccines (i.e., inactivated, attenuated or protein subunits) for a variety reasons: straightforward design and construction, heat stability, low production costs, and long-term storage capabilities (Liu et al. 2006, Human Gene Therapy 17, 1051-1061; Kurath 2005, Overview of recent DNA vaccine development for fish. In Midlyng P J, Eds. Progress in Fish Vaccinology. Karger: Basel p. 201-213). In addition, there is no risk of reversion to a pathogenic form and they have virtually no chemical impurities (Jechlinger 2006, Expert Rev. Vaccines 5, 803-825). Research on DNA vaccines fighting fish pathogens has increased steadily for the last ten years (Kurath et al. 2007, Fish rahbdovirus models for understanding host response to DNA vaccines. (Kurath G. et al., 2007, CAB Reviews: Perspectives in Agriculture, Veterinary Science, Nutrition, and Natural Resources 2, No. 048). Previous SVCV DNA vaccines designed against the European SVCV isolates have demonstrated unreliable protection and lower efficacy as compared to two other fish DNA vaccines, infectious hematopoietic necrosis virus (IHNV) and viral hemorrhagic septicemia virus (VHSV) (Shchlekunov et al. 2001, 10th International Conference of the European Association of Fish Pathologists; Dublin, Ireland p. 173; Voronova et al. 2003, 3rd International Symposium on Fish Vaccinology; Bergen, Norway, p. 103; Kurath 2005, supra; Kanellos et al. 2006, Vaccine 24, 4927-33). All three viruses, SVCV, IHNV, and VHSV, belong to the rhabdovirus family, but are separated into two different genera (Fauquet et al. 2005, Virus taxonomy—eighth report of the international committee on the taxonomy of viruses. Elsevier Academic Press, New York). IHNV and VHSV belong to the Novirhabdovirus genus of viruses whose genome contains 5 structural genes, N, M, P, G, and L, and a sixth nonvirion (NV) gene of indeterminate function. SVCV, which has tentatively been assigned to the Vesiculovirus genus, lacks the NV gene (Bjorklund et al. 1996, Virus Res. 42, 65-80; Fauquet et al. 2005, supra; Kurath 1985, supra). Phylogenetic analysis of a partial SVCV G-gene region divided isolates into four genogroups, enabling SVCV isolates from Europe (Genogroups Ib, Ic, and Id) to be distinguished from those originating from Asia (Ia) (Stone et al. 2003, Diseases of Aquatic Organisms 53, 203-210). Further phylogenetic analyses revealed that all six SVCV isolates detected in North America clustered in the SVCV Ia genogroup, suggesting that the isolates were of Asian origin (Warg et al. 2007, supra; Garver et al. 2007, J. Fish Diseases 30, 665-671). The G-gene of all three of these viruses codes for the surface glycoprotein, which is the primary antigen that the fish host mounts an immune response against and is the target insertion gene used in the DNA vaccine constructs. The novirhabdovirus DNA vaccines have demonstrated long-lasting protection with small doses in a variety of salmonid species, against various strains of the homologous virus (Corbeil et al. 2000, Vaccine 18, 2817-2824; Lorenzen and LaPatra 2005, Revue Scientifique et Technique-Office International Des Epizooties, 34, 201-213; Kurath et al. 2007, supra). In 2005 the IHNV DNA vaccine was licensed in Canada for use in the Atlantic salmon aquaculture industry and the VHSV DNA vaccine has undergone field trials at rainbow trout farms in Denmark (Liu et al. 2006, supra; Lorenzen and LaPatra 2005, supra).

To date attempts to develop an equally efficacious SVCV DNA vaccine have not been successful. Non-peer reviewed conference abstracts (Shchelkunov et al. 2001, supra, Voronova et al. 2003, supra) reported that Russian scientists developed SVCV DNA vaccines containing the G-gene insert of the European SVCV reference (Fijan) strain or a SVCV strain from Hawaii. Protection with relative percent survival (RPS) of 80% was obtained in one trial, but subsequent trials had much lower RPS or no protection. To date demonstration of protection with those vaccines has not been reproduced. More recently mixtures of 10 SVCV DNA vaccine plasmids containing partial or complete G gene fragments from the European reference strain (Fijan—Genogroup Id) have been tested in carp (Kanellos et al., 2006, supra). The majority of treatment groups had little protection, with RPS values of −11 to 33%. One group of fish receiving a combination of 3 plasmids had an RPS of 48% in a single trial, but the specific plasmid responsible for protection was not identified.

The presence of SVCV in the US and Canada has renewed research efforts to develop an effective DNA vaccine to prevent the spread and establishment of SVCV in North America. In this application is described a novel SVCV DNA vaccine utilizing the North Carolina (nc) SVCV G-gene. In order to test the vaccine a reliable challenge model was developed by testing the susceptibility of different fish host species to the North American SVCV and devising challenge treatments that induced rapid and reproducible infections in the host.

SUMMARY OF THE INVENTION

The inventors have constructed a novel DNA vaccine for control of SVCV. The vaccine construct, pSGnc, consists of a standard vector with a SVCV glycoprotein (G) gene insertion from the North Carolina isolate. In order to test the vaccine with an exotic OIE-notifiable virus, the inventors have developed a challenge model in an aquatic Biosafety Level 3 (BSL-3) laboratory utilizing a specific pathogen-free domestic koi stock.

The inventors have conducted four trial studies demonstrating that the SVCV-G DNA vaccine provided protection in vaccinated fish against challenge with the homologous virus. The protection was significant as compared to fish receiving a mock vaccine construct containing a luciferase reporter gene and to non-vaccinated controls when challenged at low, moderate, and high virus doses in fish ranging in age from 3 to 14 months. In all trials, the SVCV-G DNA immunized fish were challenged 28-days post-vaccination and experienced relative percent survivals ranging from 50 to 88%, with low mortalities varying from 10 to 50%. The non-vaccinated controls encountered high cumulative percent mortalities (CPM) from 70-100%. The luciferase mock construct vaccinated fish suffered equally high mortalities (85-100%) in all four trials. Thus the SVCV-G protein DNA vaccine offered consistent and reproducible protection in immunized fish 28 days after vaccination. This is the first report of any SVCV DNA vaccine being tested successfully in a koi fish species. These experiments prove that the SVCV DNA vaccine can elicit specific efficacious protection and validates its use as a prophylactic vaccine in ornamental koi.

Therefore, in one aspect, the present invention provides the nucleic acid encoding the entire glycoprotein (G) gene of the SVCV from North Carolina for use as DNA vaccine. The North Carolina (nc) SVCV G-gene was selected as the target gene for vaccine construction since it most closely matched the consensus G-gene sequence of the five U.S. SVCV isolates. The SVCVnc G-gene sequence has been deposited with Genbank with accession no. AY527273 and presented in SEQ ID NO: 1. The cDNA sequence was reverse transcribed from the RNA genome of SVCVnc, and the cDNA was cloned into the pcDNA3.1 vector. Selection of the proper plasmid with the correct size insert and orientation resulted in the vaccine construct pSGnc, for vaccine development.

It is another object of the present invention to provide recombinant SVCVnc G protein encoded by the nucleic acid described above, for use in diagnostic assays and for production of antibodies.

It is another object of the present invention to provide compositions comprising purified recombinant SVCVnc G protein.

It is yet another object of the present invention to provide novel vector constructs for recombinantly expressing SVCVnc G protein, as well as host cells transformed with said vector.

It is also an object of the present invention to provide a method for producing and purifying recombinant SVCVnc G protein comprising:

growing a host cell containing a vector expressing SVCVnc G in a suitable culture medium, causing expression of said vector sequence as defined above under suitable conditions for production of soluble protein and, lysing said transformed host cells and recovering said SVCVnc G protein such that it is essentially free of host toxins.

It is also an object of the present invention to provide diagnostic and immunogenic uses of the recombinant SVCVnc G protein of the present invention, as well as to provide kits for diagnostic use for example in screening for infection and confirmatory antibody tests.

It is also an object of the present invention to provide monoclonal or polyclonal antibodies, more particularly fish monoclonal antibodies which react specifically with SVCVnc G protein epitopes, either comprised in peptides or conformational epitopes comprised in recombinant proteins.

It is yet another object of the present invention to provide a SVCV vaccine comprising SVCVnc G protein of the present invention, in an amount effective to elicit an immune response in an fish against SVCV; and a pharmaceutically acceptable diluent, carrier, or excipient.

It is another object of the present invention to provide a SCVC DNA vaccine comprising a SVCVnc G-gene sequence. It is another object of the present invention to provide a method for eliciting in a subject an immune response against SVCV, the method comprising administering to a subject a DNA fragment comprising a SVCVnc G-gene sequence.

It is another object of the present invention to provide a method for eliciting in a subject an immune response against SCVC, the method comprising administering to a subject a composition comprising SVCVnc G of the present invention.

The vaccine according to the present invention is inherently safe, is not painful to administer, and should not result in adverse side effects to the vaccinated individual.

The present invention also provides vectors for the production of a recombinant SCVCnc G protein, and host cells containing the vectors.

All the objects of the present invention are considered to have been met by the embodiments as set out below.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

BRIEF DESCRIPTION OF THE DRAWINGS

FIGS. 1A, 1B, 1C, and 1D. Cumulative percent mortality (CPM) of vaccinated koi following challenge with SVCVnc. Koi were challenged 28 days after pSGnc vaccination using different virus concentrations in trials A, B, C, and D. Mortality was recorded daily during an observation period ranging of 26 to 29 days. Data shown is the average from duplicate groups for each treatment.

DETAILED DESCRIPTION

In the description that follows, a number of terms used in recombinant DNA and immunology are extensively utilized. In order to provide a clearer and consistent understanding of the specification and claims, including the scope to be given such terms, the following definitions are provided.

In general, an 'epitope' is defined as a linear array of 3-10 amino acids aligned along the surface of a protein. In a linear epitope, the amino acids are joined sequentially and follow the primary structure of the protein. In a conformational epitope, residues are not joined sequentially, but lie linearly along the surface due to the conformation (folding) of the protein. With respect to conformational epitopes, the length of the epitope-defining sequence can be subject to wide variations. The portions of the primer structure of the antigen between the residues defining the epitope may not be critical to the structure of the conformational epitope. For example, deletion or substitution of these intervening sequences may not affect the conformational epitope provided sequences critical to epitope conformation are maintained (e.g. cysteines involved in disulfide bonding, glycosylation sites, etc.). A conformational epitope may also be formed by 2 or more essential regions of subunits of a homo-oligomer or hetero-oligomer. As used herein, 'epitope' or 'antigenic determinant' means an amino acid sequence that is immunoreactive. As used herein, an epitope of a designated polypeptide denotes epitopes with the same amino acid sequence as the epitope in the designated polypeptide, and immunologic equivalents thereof. Such equivalents also include strain, subtype (=genotype), or type (group)-specific variants, e.g. of the currently known sequences or strains belonging to SVCV strains or field isolates.

The term 'solid phase' intends a solid body to which the individual SVCV G protein antigen is bound covalently or by noncovalent means such as hydrophobic, ionic, or van der Waals association.

The term 'biological sample' intends a fluid or tissue of a mammalian individual (e.g. an anthropoid, a human), reptilian, aquatic, avian, or any other zoo or farm animal that commonly contains antibodies produced by the individual, more particularly antibodies against SVCV. The fluid or tissue may also contain viral antigens. Such components are known in the art and include, without limitation, blood, plasma, serum, urine, spinal fluid, lymph fluid, secretions of the respiratory, intestinal or genitourinary tracts, tears, saliva, milk, white blood cells and myelomas. Body components include biological liquids. The term 'biological fluid' refers to a fluid obtained from an organism.

The term 'immunologically reactive' means that the antigen in question will react specifically with anti-G protein antibodies present in a body component from a SVCV infected individual.

The term 'immune complex' intends the combination formed when an antibody binds to an epitope on an antigen.

The term 'purified' as applied to proteins herein refers to a composition wherein the desired protein comprises at least 35% of the total protein component in the composition. The desired protein preferably comprises at least 40%, more preferably at least about 50%, more preferably at least about 60%, still more preferably at least about 70%, even more preferably at least about 80%, even more preferably at least about 90%, and most preferably at least about 95% of the total protein component. The composition may contain other compounds such as carbohydrates, salts, lipids, solvents, and the like, without affecting the determination of the percentage purity as used herein. An 'isolated' G protein intends a SVCV surface glycoprotein composition that is at least 35% pure.

The term 'essentially purified proteins' refers to proteins purified such that they can be used for in vitro diagnostic methods and as a prophylactic compound. These proteins are substantially free from cellular proteins, vector-derived proteins or other SVCV components. The proteins of the present invention are purified to homogeneity, at least 80% pure, preferably, 90%, more preferably 95%, more preferably 97%, more preferably 98%, more preferably 99%, even more preferably 99.5%.

The term 'recombinantly expressed' used within the context of the present invention refers to the fact that the proteins of the present invention are produced by recombinant expression methods be it in prokaryotes, or lower or higher eukaryotes as discussed in detail below.

The term 'lower eukaryote' refers to host cells such as yeast, fungi and the like. Lower eukaryotes are generally (but not necessarily) unicellular. Preferred lower eukaryotes are yeasts, particularly species within *Saccharomyces, Schizosaccharomyces, Kluveromyces, Pichia* (e.g. *Pichia pastoris*), *Hansenula* (e.g. *Hansenula polymorpha, Yarowia, Schwaniomyces, Schizosaccharomyces, Zygosaccharomyces* and the like. *Saccharomyces cerevisiae, S. carlsberoensis* and *K. lactis* are the most commonly used yeast hosts, and are convenient fungal hosts.

The term 'prokaryotes' refers to hosts such as *E. coli, Lactobacillus, Lactococcus, Salmonella, Streptococcus, Bacillus subtilis* or *Streptomyces*. Also these hosts are contemplated within the present invention.

The term 'higher eukaryote' refers to host cells derived from higher animals, such as mammals, reptiles, fish, insects, and the like. Presently preferred higher eukaryote host cells are derived from fish (e.g. epithelioma papulosum cyprini), Chinese hamster (e.g. CHO), monkey (e.g. COS and Vero cells), baby hamster kidney (BHK), pig kidney (PK15), rabbit kidney 13 cells (RK13), the human osteosarcoma cell line 143 B, the human cell line HeLa and human hepatoma cell lines like Hep G2, and insect cell lines (e.g. *Spodoptera frugiperda*). The host cells may be provided in suspension or flask cultures, tissue cultures, organ cultures and the like. Alternatively the host cells may also be transgenic animals.

The term 'polypeptide' refers to a polymer of amino acids and does not refer to a specific length of the product; thus, peptides, oligopeptides, and proteins are included within the definition of polypeptide. This term also does not refer to or exclude post-expression modifications of the polypeptide, for example, glycosylations, acetylations, phosphorylations and the like. Included within the definition are, for example, polypeptides containing one or more analogues of an amino acid (including, for example, unnatural amino acids, PNA, etc.), polypeptides with substituted linkages, as well as other modifications known in the art, both naturally occurring and non-naturally occurring.

The term 'recombinant polynucleotide or nucleic acid' intends a polynucleotide or nucleic acid of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The term 'recombinant host cells', 'host cells', 'cells', 'cell lines', 'cell cultures', and other such terms denoting microorganisms or higher eukaryotic cell lines cultured as unicellular entities refer to cells which can be or have been, used as recipients for a recombinant vector or other transfer polynucleotide, and include the progeny of the original cell which has been transfected. It is understood that the progeny of a single parental cell may not necessarily be completely identical in morphology or in genomic or total DNA complement as the original parent, due to natural, accidental, or deliberate mutation.

The term 'replicon' is any genetic element, e.g., a plasmid, a chromosome, a virus, a cosmid, etc., that behaves as an autonomous unit of polynucleotide replication within a cell; i.e., capable of replication under its own control.

The term 'vector' is a replicon further comprising sequences providing replication and/or expression of a desired open reading frame.

The term 'control sequence' refers to polynucleotide sequences which are necessary to effect the expression of coding sequences to which they are ligated. The nature of such control sequences differs depending upon the host organism; in prokaryotes, such control sequences generally include promoter, ribosomal binding site, and terminators; in eukaryotes, generally, such control sequences include promoters, terminators and, in some instances, enhancers. The term 'control sequences' is intended to include, at a minimum, all components whose presence is necessary for expression, and may also include additional components whose presence is advantageous, for example, leader sequences which govern secretion.

The term 'promoter' is a nucleotide sequence which is comprised of consensus sequences which allow the binding of RNA polymerase to the DNA template in a manner such that mRNA production initiates at the normal transcription initiation site for the adjacent structural gene.

The expression 'operably linked' refers to a juxtaposition wherein the components so described are in a relationship permitting them to function in their intended manner. A control sequence 'operably linked' to a coding sequence is ligated in such a way that expression of the coding sequence is achieved under conditions compatible with the control sequences.

An 'open reading frame' (ORF) is a region of a polynucleotide sequence which encodes a polypeptide and does not contain stop codons; this region may represent a portion of a coding sequence or a total coding sequence.

A 'coding sequence' is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include but is not limited to mRNA, DNA (including cDNA), and recombinant polynucleotide sequences.

The term 'immunogenic' refers to the ability of a substance to cause a humoral and/or cellular response, whether alone or when linked to a carrier, in the presence or absence of an adjuvant. 'Neutralization' refers to an immune response that blocks the infectivity, either partially or fully, of an infectious agent. A 'vaccine' is an immunogenic composition capable of eliciting protection against disease, whether partial or complete. A vaccine may also be useful for treatment of an infected individual, in which case it is called a therapeutic vaccine.

The term 'therapeutic' refers to a composition capable of treating SVCV infection. The term 'effective amount' for a therapeutic or prophylactic treatment refers to an amount of epitope-bearing polypeptide sufficient to induce an immunogenic response in the individual to which it is administered, or to otherwise detectably immunoreact in its intended system (e.g., immunoassay). Preferably, the effective amount is sufficient to effect treatment, as defined above. The exact amount necessary will vary according to the application. For vaccine applications or for the generation of polyclonal antiserum/antibodies, for example, the effective amount may vary depending on the species, age, and general condition of the individual, the severity of the condition being treated, the particular polypeptide selected and its mode of administration, etc. It is also believed that effective amounts will be found within a relatively large, non-critical range. An appropriate effective amount can be readily determined using only routine experimentation.

Before explaining the present invention in detail, it is important to understand that the invention is not limited in its application to the details of the construction illustrated and the steps described herein. The invention is capable of other embodiments and of being practiced or carried out in a variety of ways. It is to be understood that the phraseology and terminology employed herein is for the purpose of description and not of limitation.

The present invention provides a novel DNA vaccine and methods designed to protect against SVCV. The invention is directed to DNA-mediated vaccination and it preferably involves the introduction of a nucleic acid comprising DNA encoding glycoprotein (G) of SVCV or epitopes thereof selected from any SVCV strain, such that the G protein is expressed within cells of the vaccinated subject. Preferably, the G protein is from a North America SVCV isolates which include Wisconsin, Illinois, Washington, Missouri, and Lake Ontario, Canada. The gene encoding the G protein of each of these isolates has been sequenced and is publicly available. More preferably, the G protein sequence is from the North Carolina strain, since it is closest to the consensus sequence when comparing all the US SVCV G-gene sequences. Other known and yet to be discovered SVCV strains characterized as belonging to Genogroup I with G-gene region identities from 82.7-100% (Stone et al., 2003, supra) could provide protective epitopes as described in the present invention and therefore are part of the present invention.

Preferably, the isolated G protein encoding sequence from SVCV North Carolina is defined by the nucleotide sequence of SEQ ID NO:1. As contemplated herein, in one aspect, the invention includes the G-gene sequence of other strains and analogs, fragments, mutants, substitutions, synthetics, or variants thereof that effectively encode G protein from SVCV North Carolina, its epitopes, and/or mimetics. The SVCV G nucleic acid encodes the complete antigen, or a portion thereof, containing functional fragments thereof (e.g. fragments which are not missing sequence essential to the formation or retention of an epitope necessary for a protective immune response against SVCV). As a result, in one aspect, the invention encompasses DNA sequences which encode for and/or express in appropriate transformed cells, proteins which may be the full length antigen, antigen fragment, antigen derivative or a fusion product of such antigen, antigen fragment or antigen derivative with another protein. G-protein amino acid identity between SVCV U.S. isolates and the European reference strain (Fijian/subgenogroup Id) range between 94.3 and 95.1% (Warg et al., 2007, supra). This suggests that cross protection by the SVCVnc DNA vaccine against other SVCV isolates from the four sub-genogroups (Ia, Ib, Ic, and Id) as well as other yet to be discovered strains or genogroups which share G-protein sequence homology is likely.

The inventive vaccine may be administered alone or in combination with additional antigenic components known to those skilled in the art.

As defined herein an "isolated" DNA is one which is substantially separated from other cellular components which naturally accompany a native sequence. The term embraces a nucleic acid sequence that has been removed from its naturally occurring environment, and includes recombinant or cloned DNA isolates and chemically synthesized analogs or analogs biologically synthesized.

The DNA encoding the desired antigen can be introduced into a host cell in any suitable form including, the fragment alone, a linearized plasmid, a circular plasmid, a plasmid capable of replication, an episome, RNA, etc. Preferably, the gene is contained in a plasmid. In a particularly preferred embodiment, the plasmid is an expression vector. Individual expression vectors capable of expressing the genetic material can be produced using standard recombinant techniques. Please see e.g., Maniatis et al., 1985 *Molecular Cloning: A Laboratory Manual* or *DNA Cloning*, Vol. I and II (D. N. Glover, ed., 1985) for general cloning methods.

The DNA, alone or in a vector, can be delivered by any method which can be used to deliver DNA as long as the DNA is expressed and the desired antigen is made in the cell. Methods include, without limitation, injection into the tissue of the recipient, oral, oral administration may be in the form of an ingestable liquid or solid formulation, or pulmonary delivery and inoculation by particle bombardment (i.e., gene gun) after coating a carrier particle with the DNA vaccine.

The vector, used for inserting the polynucleotide encoding the desired vaccine antigen, of which numerous ones are known in the art, is by itself "inert" (not eliciting immunity to itself), can easily be introduced to the recipient (to elicit immunity to the insert), and does not integrate into the host chromosome. Various vectors and delivery systems are known in the art. Preferred vectors are the pVAX1 and pcDNA3.1 eukaryotic expression vectors commercially available from Invitrogen, Carlsbad, Calif. Therefore, the present invention relates more particularly to the SCVCnc G protein nucleic acid sequence in a vector, specifically, pSGnc. Other plasmids containing a promoter for expression of the inserted gene in its host may be used such as the Flexi™ system by Promega, the QIAexpress™ Expression System by Qiagen, the Radiance™ Cloning and Expression System from Novagen, to name a few.

The present invention also contemplates host cells transformed with a recombinant vector as defined above. In a preferred embodiment, *E. coli* strain is employed. Methods for introducing vectors into cells are known in the art. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. Host cells provided by this invention include *E. coli* containing a vector comprising the SVCV G-gene sequence. Eukaryotic hosts include lower and higher eukaryotic hosts as described in the definitions section. Lower eukaryotic hosts include yeast cells well known in the art. Higher eukaryotic hosts mainly include fish cell lines, epithelioma paulosum cyrprini (EPC) cell line and mammalian cell lines known in the art and include many immortalized cell lines available from the ATCC, including HeLa cells, Chinese hamster ovary (CHO) cells, Baby hamster kidney (BHK) cells, PK15, RK13 and a number of other cell lines.

The vaccine of the present invention may include nucleic acid sequences that regulate the expression of the SVCV G protein encoding sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e. ATG) in front of a protein-encoding gene, splicing signal for introns, maintenance of the correct reading frame of that gene to permit proper translation of mRNA, and stop codons.

The inventive vaccine further comprises a pharmacologically acceptable carrier or diluent. Suitable carriers for the vaccine are well known to those skilled in the art and include but are not limited to proteins, sugars, etc. Such carriers may be aqueous or non aqueous solutions, suspensions, and emulsions. Examples of non-aqueous carriers are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose and sodium chloride, lactated Ringer's or fixed oils. Intravenous vehicles include fluid and nutrient replenishers, electrolyte replenishers ushc as those based on Ringer's dextrose, and the like. Preservatives and antimicrobials, antioxidants, chelating agents, inert gases and the like. Preferred preservatives include formalin, thimerosal, neomycin, polymyxin B and amphotericin B.

The term "adjuvant" refers to a compound or mixture that enhances the immune response and/or promotes the proper rate of absorption following inoculation, and as used herein, encompasses any uptake-facilitating agent. Previous research in fish DNA vaccine has indicated that an adjuvant is not usually required for a proper immune response. However, if necessary, acceptable adjuvants include, but are not limited to, complete Freund's adjuvant, incomplete Freund's adjuvant, saponin, mineral gels such as aluminum hydroxide, surface active substances such as lysolecithin, pluronic plyols, polyanions, peptides, oil or hydrocarbon emulsions, keyhole limpet hemocyanins, dinitrophenol, and others.

The method comprises administering to the subject an effective immunizing dose of the vaccine of the present invention. For purposes of this invention, an "effective immunizing amount" of the vaccine of the present invention is at least 0.001 ug DNA per kilogram of body weight, with a range of 0.01-10.0 ug/g for fish. The DNA alone or in a vector, can be delivered by any method which can be used to deliver DNA as long as the DNA is expressed and the desired antigen is made in the cell. Methods include, without limitation, injection into the tissue of the recipient, intradermal, ocular, oral, oral administration may be in the form of an ingestable liquid or solid formulation, or pulmonary delivery and inoculation by particle bombardment (i.e. gene gun) after coating a carrier particle with the DNA vaccine.

The treatment may be given in a single dose schedule, or preferably a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Typically in fish, a single dose provides adequate long term protection, but a booster may be required dependent on the longevity of the fish. Other schedules sufficient to elicit the desired responses expected to reduce disease symptoms, or reduce severity of disease may be used.

The present invention further relates to a composition comprising SVCV G protein for use in in vitro detection of SVCV antibodies present in a biological sample.

For in vitro detection of SCVC antibodies present in a biological sample, the assay may comprise at least (i) contacting said biological sample with a composition comprising any of the SVCV G proteins or peptides derived from said protein which are immunologically identifiable with SVCV G protein, preferably in an immobilized form under appropriate conditions which allow the formation of an immune complex, wherein said peptide or protein can be a biotinylated peptide or protein which is covalently bound to a solid substrate by means of streptavidin or avidin complexes, (ii) removing unbound components, (iii) incubating the immune complexes formed with heterologous antibodies, with said heterologous antibodies having conjugated to a detectable label under appropriate conditions, and (iv) detecting the presence of said immune complexes visually or mechanically (e.g. by means of densitometry, fluorimetry, colorimetry).

The present invention also relates to a kit for determining the presence of SCVC antibodies, in a biological sample, comprising:

at least one peptide or protein composition as defined above, possibly in combination with other polypeptides or peptides from SVCV or other types of virus antigens, with said peptides or proteins being preferentially immobilized on a solid support, more preferably on different microwells of the same ELISA plate, and even more preferentially on one and the same membrane strip, a buffer or components necessary for producing the buffer enabling binding reaction between these polypeptides or peptides and the antibodies against SVCV present in the biological sample, means for detecting the immune complexes formed in the preceding binding reaction, and possibly also including an automated scanning and interpretation device for inferring the virus present in the sample from the observed binding pattern.

The immunoassay methods according to the present invention utilize SCVC domains that maintain linear (in case of peptides) and conformational epitopes (proteins) recognized by antibodies in the sera from individuals infected with a SCVC. SCVC antigens of the present invention may be employed in virtually any assay format that employs a known antigen to detect antibodies. A common feature of all of these assays is that the antigen is contacted with the body component suspected of containing SVCV antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin or streptavidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immunolon™), diazotized paper, nylon membranes, activated beads, and Protein A beads. For example, Dynatech Immunolon™ or Immunlon™ 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogeneous format, the test sample is incubated with the combination of antigens in solution. For example, it may be under conditions that will precipitate any antigen-antibody complexes that are formed. Both standard and competitive formats for these assays are known in the art.

In a standard format, the amount of SVCV antibodies in the antibody-antigen complexes is directly monitored. In a competitive format, the amount of SVCV antibodies in the sample is deduced by monitoring the competitive effect on the binding of a known amount of labeled antibody (or other competing ligand) in the complex.

Complexes formed comprising antibody (or in the case of competitive assays, the amount of competing antibody) are detected by any of a number of known techniques, depending on the format.

In an immunoprecipitation or agglutination assay format the reaction between the SCVC antigens and the antibody forms a network that precipitates from the solution or suspension and forms a visible layer or film of precipitate. If no anti-SCVC antibody is present in the test specimen, no visible precipitate is formed.

The SVCV vaccine, proteins, peptides, or antigens of the present invention will typically be packaged in the form of a kit for use in these immunoassays. The kit will normally contain in separate containers the SVCV vaccine, antigen, control antibody formulations (positive and/or negative), labeled antibody when the assay format requires the same and signal generating reagents (e.g. enzyme substrate) if the label does not generate a signal directly. The SVCV G protein antigen may be already bound to a solid matrix or separate with reagents for binding it to the matrix. Instructions (e.g. written, tape, CD-ROM, etc.) for carrying out the assay usually will be included in the kit. Immunoassays that utilize the SVCV G protein antigen are useful in screening subjects potentially harboring SVCV.

The present invention further contemplates the use of SVCV G protein antigen, or parts thereof as defined above, for in vitro monitoring SVCV infection or prognosing the response to treatment of subject with SVCV infection by:

incubating a biological sample from an infected subject with SVCV G protein or a suitable part thereof under conditions allowing the formation of an immunological complex, removing unbound components, calculating the anti-SVCV G protein titers present in said sample (for example at the start of and/or during the course of treatment), and monitoring the natural course of infection, or prognosing the response to treatment of said fishon the basis of the amount anti-SVCV G protein titers found in said sample at the start of treatment and/or during the course of treatment.

A decrease of 2, 3, 4, 5, 7, 10, 15, or preferably more than 20 times of the initial anti-SVCV G protein titers could be concluded to be long-term, sustained responders to treatment.

It is to be understood that smaller fragments of the above-mentioned peptides also fall within the scope of the present invention. Said smaller fragments can be easily prepared by chemical synthesis and can be tested for their ability to be used in an assay as detailed above.

The present invention also relates to a kit for monitoring SVCV infection or prognosing the response to treatment of infected fish comprising:

at least one SVCV G protein or peptide as defined above, a buffer or components necessary for producing the buffer enabling the binding reaction between these proteins or peptides and the anti-SVCV G protein antibodies present in a biological sample, means for detecting the immune complexes formed in the preceding binding reaction, and possibly also an automated scanning and interpretation device for inferring a decrease of anti-SVCV G protein titers during the progression of treatment.

The present invention also relates to a G protein specific antibody raised upon immunizing an animal with a peptide or protein composition, with said antibody being specifically reactive with any of the polypeptides or peptides as defined above, and with said antibody being preferably a monoclonal antibody.

The G protein specific monoclonal antibodies of the invention can be produced by any hybridoma liable to be formed according to classical methods from splenic or lymph node cells of an animal, immunized against the G protein or peptides according to the invention, as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

Alternatively, the present invention also relates to the use of any of the above-specified G protein monoclonal antibodies for the preparation of an immunoassay kit for detecting the presence of G protein antigen in a biological sample, for the preparation of a kit for prognosing/monitoring of SVCV infection or for the preparation of a SVCV medicament.

The present invention also relates to a method for in vitro diagnosis or detection of SVCV G protein antigen present in a biological sample, comprising at least (i) contacting said biological sample with any of the SVCV G protein specific monoclonal antibodies as defined above, preferably in an immobilized form under appropriate conditions which allow the formation of an immune complex, (ii) removing unbound components, (iii) incubating the immune complexes formed with heterologous antibodies, which specifically bind to the antibodies present in the sample to be analyzed, with said heterologous antibodies conjugated to a detectable label under appropriate conditions, and (iv) detecting the presence of said immune complexes visually or mechanically (e.g. by means of densitometry, fluorimetry, colorimetry).

The present invention also relates to a kit for in vitro diagnosis of a G protein antigen present in a biological sample, comprising:

at least one monoclonal antibody as defined above, with said antibody being preferentially immobilized on a solid substrate, a buffer or components necessary for producing the buffer enabling binding reaction between these antibodies and the G protein antigens present in the biological sample, and a means for detecting the immune complexes formed in the preceding binding reaction.

The kit can possibly also include an automated scanning and interpretation device for inferring the viral antigens present in the sample from the observed binding pattern.

Monoclonal antibodies according to the present invention are suitable both as therapeutic and prophylactic agents for treating or preventing SVCV infection in susceptible SVCV subjects. Subjects include fish and shrimp.

In general, this will comprise administering a therapeutically or prophylactically effective amount of one or more monoclonal antibodies of the present invention to a susceptible subject or one exhibiting SVCV infection. Any active form of the antibody can be administered, including Fab and F(ab')₂ fragments. Antibodies of the present invention can be produced in any system, including insect cells, baculovirus expression systems, fish, chickens, rabbits, goats, cows, or plants such as tomato, potato, banana or strawberry. Methods for the production of antibodies in these systems are known to a person with ordinary skill in the art. Preferably, the antibodies used are compatible with the recipient species such that the immune response to the MAbs does not result in clearance of the MAbs before virus can be controlled, and the induced immune response to the MAbs in the subject does not induce "serum sickness" in the subject. Preferably, the MAbs administered exhibit some secondary functions such as binding to Fc receptors of the subject.

Treatment of individuals having SVCV infection may comprise the administration of a therapeutically effective amount of G protein antibodies of the present invention. The antibodies can be provided in a kit as described below. The antibodies can be used or administered as a mixture, for example in equal amounts, or individually, provided in sequence, or administered all at once. In providing a patient with antibodies, or fragments thereof, capable of binding to G protein, or an antibody capable of protecting against SVCV in a recipient patient, the dosage of administered agent will vary depending upon such factors as the patient's age, weight, height, sex, general medical condition, previous medical history, etc.

In general, it is desirable to provide the recipient with a dosage of antibody which is in the range of from about 1 pg/kg-100 pg/kg, 100 pg/kg-500 pg/kg, 500 pg/kg-1 ng/kg, 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg, 500 mg/kg-1 g/kg, 1 g/kg-5 g/kg, 5 g/kg-10 g/kg (body weight of recipient), although a lower or higher dosage may be administered.

Active immunization can be induced by administering one or more antigenic and/or immunogenic epitopes as a component of a subunit vaccine. Vaccination could be performed orally or parenterally in amounts sufficient to enable the recipient to generate protective antibodies against this biologically functional region, prophylactically or therapeutically. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cyteine and derivatives thereof. Alternative protein modification techniques may be used e.g., NH₂-acetylation or COOH-terminal amidation, to provide additional means for coupling or fusing the peptide to another protein or peptide molecule or to a support.

The antibodies capable of protecting against SVCV are intended to be provided to recipient subjects in an amount sufficient to effect a reduction in the SVCV infection symptoms. An amount is said to be sufficient to "effect" the reduction of infection symptoms if the dosage, route of administration, etc. of the agent are sufficient to influence such a response. Responses to antibody administration can be measured by analysis of subject's vital signs.

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Fish Stocks

Goldfish (*Carassius auratus*) less than year old and 7-10 cm in length were shipped from Pool Fisheries, Inc. (Lonoke, Ark.) to the wet laboratory facility at the Western Fisheries Research Center (WFRC, Seattle, Wash.). Fish were housed in tanks with flow-through sand-filtered and UV-treated fresh water at water temperatures of 16-18° C. Fish were monitored daily and fed every other day Wardley Ten floating pellets (Hartz Mountain Co.). Goldfish were maintained in the stock tanks until commencement of the SVCV susceptibility challenges.

Koi (*Cyprinus carpio* koi) from a specific pathogen-free domestic stock were obtained from a local koi farm (Pan Intercorp., Kenmore, Wash.). The koi distributor annually breeds his own koi stock. The breeder has voluntarily participated in the United States Department of Agriculture (USDA) Animal and Plant Health Inspection Service (APHIS) screening program for SVCV in ornamental fish and is the first US koi distributor with a USDA APHIS-certified SVCV quarantine facility for any imported fish arriving at the facility. One month-old pathogen-free domestic koi were transferred to the wet laboratory facility at the WFRC and reared under the same conditions described for the goldfish. Koi were also fed every other day, but received a mixed feed diet of moist and dry pellets consisting of Life Stage Diet Food (Oregon Biodiet, Longview, Wash.), Wardley Pond 10 (Hartz Mountain Co., Secaucus, N.J.), and Hikari Gold (Kyorin Food Industries, Minami-mani, Himeji, Japan). The amount, pellet size, and type of feed varied as the koi aged. Koi were held in stock tanks until initiation of the susceptibility challenges, cold stress challenge experiment, or vaccine trial studies.

Virus Propagation

The North American SVCV isolate from North Carolina (SVCVnc) (Goodwin, 2002, J. Aquatic Animal Health 14, 161-161) was propagated in an epithelioma papulosum cyprini (EPC) cell line (Fijan et al. 1983, Annales de l'Institut Pasteur Virologie, 134E, 207-220) at a constant temperature of 20° C. in minimum essential medium (MEM; Invitrogen Inc. Carlsbad, Calif.) supplemented with 10% fetal bovine serum (Hyclone Inc., Logan, Utah) and 2 mM L-glutamine (Invitrogen Inc.), and buffered to pH 7.0 with 7.5% sodium bicarbonate (Fisher Scientific Co., Pittsburgh, Pa.). Virus titers for the challenge inocula were determined by plaque assay following the procedure outlined by Batts and Winton (1989, J. Aquatic Animal Health 1, 284-290) with a modified incubation temperature of 20° C.

Susceptible Challenges of Goldfish and Koi

Prior to challenge, fish were transferred to an aquatic biosafety level 3 (BSL-3) laboratory housed in a separate building from the main WFRC wet laboratory. Due to OIE listing of SVCV and its exotic pathogen status in North America all in vivo challenges adhered to aquatic BSL-3 containment regulations. After transfer to the BSL-3 at 16-18° C., water temperature was decreased 1° C. daily until tank water temperatures reached 10-12° C. Fish were then acclimated at this colder temperature for an additional five days.

For the injection challenge, fish were anaesthetized by immersion in 100 µg/ml of tricaine methane sulfonate (MS-222; Argent Chemical Laboratories) buffered with sodium bicarbonate to a pH of 7.5. All injection-challenged fish received a 100 µL volume of viral supernatant via an intraperitoneal injection (IP). After injection fish were transferred to a recovery tank until consciousness and swimming mobility were regained. A mock injection challenge of an equivalent volume of MEM-10 media was also included for all susceptibility experiments. Fish challenged at various virus concentrations by immersion were held in a volume of 3 L for one hour with aeration after which intake water flow was resumed. Mock immersion challenges occurred under the same conditions, but an equivalent volume of MEM-10 culture medium was added into the water instead of virus. All mock and virus challenge treatments were done duplicate tanks. Injection and immersion challenges were terminated after 30 days and fish were fed every other day during the challenge. Dead fish were removed daily and mortalities were recorded. Fisher's exact test was performed to confirm that there was no statistically significant difference between mortalities occurring in the duplicate treatment tanks. Average cumulative percent mortality (CPM) was calculated as the number of fish that died from the pooled duplicate tanks divided by the total number fish receiving that treatment X 100.

Goldfish of an average weight of 14.6 g were exposed to SVCVnc in two susceptibility experiments. Each experiment consisted of immersion challenges at virus doses of $1 \times 10^3$ PFU/ml, $1 \times 10^4$ PFU/ml, and $1 \times 10^5$ PFU/ml, and one injection challenge with each fish receiving $1 \times 10^6$ PFU. There were 15 goldfish in each duplicate treatment group for each experiment.

One month-old koi weighing on average 0.94 g were also challenged with SVCVnc in two experiments. The first preliminary experiment challenged three koi each by immersion at $1 \times 10^5$ PFU/ml or by injection with $1 \times 10^6$ PFU/fish. The second experiment used the same challenge protocols and doses, but with duplicate treatment groups of 10 koi each. Two koi each from the immersion and injection challenge treatment groups from the second experiment were titered for virus. Virus quantification in whole fish homogenate samples was done by plaque assay following the methods described by Batts and Winton (1989, supra). Virus titers were shown as the logarithmic geometric mean of the virus concentration in PFU/g for virus-positive fish in each treatment group.

Cold Stress Challenges in Koi

The morbidity outcome of koi subjected to two different cold water temperature stressors prior to virus challenges were compared. It has been reported that exposure of fish to a cold temperature stress treatment prior to SVCV challenge is important for disease initiation (Ahne 1986, Veterinary Immunology and Immunopathology 12, 383-386). One challenge protocol used the cold stressor that was described previously in the species susceptibility testing, in which fish were slowly acclimated to colder water temperatures (10-12° C.) and held at that temperature for several days. This slow acclimation to colder water temperatures takes approximately 14 days before the challenge can be initiated. The other treatment tested was a rapid cold water stressor, in which fish were transferred on the same day of challenge from stock water temperatures of 16-18° C. to challenge temperatures of 10-12° C. Duplicate groups of 10 koi at 3.5 months of age and weighing 3.5 g were subjected to each cold water stress treatment. Fish were then challenged either by immersion or injection using the same challenge doses and methods describe for koi in the susceptibility experiments. After challenge the BSL-3 laboratory water temperature was raised 0.5° C. a day until the temperature reached 14° C. and remained at that temperature for the duration of the experiment. The CPM and the mean day to death (MDD) were the parameters used to compare cold water stress treatments. MDD was the sum of the number of days post-challenge that each fish died on divided by the total number of mortalities for a particular treatment. A proportion of the survivors and dead fish were screened for virus by plaque assay following the previously cited protocol.

Vaccine Construction

The entire glycoprotein (G) gene of the SVCV from North Carolina was sequenced (Genbank AY527273 by Emmenegger in 2004) following the protocols previously described by Emmenegger et al. (2000, Diseases of Aquatic Organisms 40, 163-176), utilizing conserved G-gene primers designed against European SVCV strains (Bjorklund, et al. 1995, Veterinary Research 26, 394-398; Bjorklund et al. 1996, Virus Research 42, 65-80; Stone et al. 2003, Diseases of Aquatic Organisms 53, 203-310). The North Carolina (nc) SVCV G-gene was selected as the target gene for vaccine construction, since it most closely matched the consensus G-gene sequence of the five U.S. SVCV isolates (data not shown). Total RNA from SVCVnc viral stock was extracted with Trizol reagent (Invitrogen Inc.) according to manufacturer's instructions and resuspended in 50 µL of enzyme-grade water.

Specific SVCVnc G-gene forward (5'-CACCATGTCTAT-CATCAGCTACATC-3' (SEQ ID NO:2) and reverse (5'-CTAAACGAAGGACCGCATTTCGTG-3", SEQ ID NO:3) cloning primers were designed to facilitate directional cloning of the cDNA generated by reverse transcription (RT) and polymerase chain reaction (PCR), following the procedures described by Emmenegger et al. (2003, Virus Research 96, 15-25). The blunt-end amplified products were directionally cloned into the pcDNA3.1 vector using the TOPO™ expression kit (Invitrogen Inc.) following the manufacturer's instructions. Transformed clones with the targeted insert were selected by the rapid colony PCR protocol (Novagen) utilizing vector primers (T7 and reverse BGH) (Invitrogen), and internal SVCV G-gene primers 379+ (5'-TTTCCCCCT-CAAAGTTGCGG-3', SEQ ID NO:4) and 978⁻/F1 (5'-TCT-TGGAGCCAAATAGCTCARRTC-3, SEQ ID NO:5). A restriction enzyme digest was performed to confirm the correct size and orientation of the inserts (data not shown). One clone was selected for further vaccine development and henceforth will be referred to as pSGnc (SVCV DNA) vaccine. The entire G-gene nucleotide sequence of the pSGnc construct was determined to verify that no sequence changes had occurred during RT/PCR and cloning. The control mock vaccine (pLuc) containing the luciferase reporter gene in the pCDNA-3.1 vector was produced earlier by Corbeil et al. (1999, Diseases of Aquatic Organisms 39, 29-36; 2000, Vaccine 18, 2817-2824). Both plasmid constructs were propagated in *Escherichia coli* and purified by an alkaline lysis methodology described by Saporito-Irwin et al. (1997, Biotechniques 23, 424-427), as used previously with the IHNV DNA vaccine (Corbeil et al. 2000, supra).

Vaccination

In each of the four trial experiments (A, B, C, and D) there were three treatment groups: the SVCV DNA vaccine (pSGnc), the mock luciferase vaccine (pLuc), and a non-vaccinated (NV) control. The NV control treatment group fish received no injection and were transferred from the stock tanks to a separate holding tank receiving the same water source as the injected fish. Average fish weights and ages at vaccination for the four trials are shown in Table 1. Prior to vaccination all fish were anaesthetized as previously described. Each fish received a 10 µg vaccine dose in a 50 µL inoculum volume of phosphate buffered saline (PBS) via an intramuscular (IM) injection in the epaxial muscle midway between the posterior end of the dorsal fin and lateral line.

After recovery, all fish from each treatment group were transferred to separate holding tanks for 28 days at a water temperature of 19-20°. Vaccinated fish were monitored daily and fed every other day.

Virus Challenge after Vaccination

Twenty-eight days post-vaccination fish were transferred to the aquatic biosafety level 3 (BSL-3) laboratory. All koi were subjected to a rapid cold-water stressor (i.e. transfer from stock water temperatures of 19-20° C. to challenge water temperatures of 10-12° C.) prior to virus challenge. For viral challenge, fish were injected IP with 100 μL of viral supernatant after anaesthetizing the fish as previously described. The homologous virus strain (SVCV North Carolina) that was utilized in the DNA vaccine construct was used in all challenges. Challenge doses are shown in Table 1. A mock challenge, as previously described, was also included for each treatment group for all trial experiments. Each mock and viral-challenged treatment group was divided into duplicate groups of 10 fish/tank. The BSL-3 laboratory water temperature on the day of challenge was 10-12° C. and was raised 0.5° C. a day until the temperature reached 14° C. The challenge conditions of each trial are outlined in Table 1.

Fish health was monitored daily and fish were fed every other day for a 26-29 day observation period. Dead fish were removed from the tank, and stored at −80° C. Efficacy of the SVCV DNA vaccine was assessed by comparing the cumulative percent mortality (CPM), and relative percent survival (RPS) between treatment groups. RPS values were calculated using the following formula: (1-CPM of vaccinated group/CPM of the negative control) X 100 (Johnson et al. 1982, Journal of Fish Disease 5, 197-205). Virus titers of sampled dead fish and survivors, and the mean day to death (MDD) of the mortalities from each of the treatment groups were also used to evaluate vaccine performance. Fisher's exact test was used to confirm that there was no statistically significant difference between mortalities in the duplicate treatment tanks. Survival curves were calculated by Kaplan-Meier analysis to assess differences between treatment groups. The Mantel-Cox Log-rank test (Systat 8.0) determined if the resultant survivor curves were significantly different. Forty-five percent of the mortalities from trials A & B, and all mortalities from trials C & D were screened for virus. A proportion of the survivors were also sampled for virus quantification. Virus quantification of whole fish samples were processed blind by plaque assay as previously described.

TABLE 1 pSGnc DNA vaccine trial challenge conditions

| Tri | Koi weight | Koi Age | Challenge Dose | Season |
|---|---|---|---|---|
| A | 1.5 | 4.0 | $5.0 \times 10^4$ | February 2006 |
| B | 1.5 | 4.0 | $1.0 \times 10^6$ | February 2006 |
| C | 3.5 | 10.5 | $1.0 \times 10^5$ | April 2006 |
| D | 4.3 | 10-14.5 | $1.0 \times 10^5$ | July 2006 |

[a]Weight and age are at time of vaccination with 10 ug dose of pSGnc DNA vaccine
[b]Fish received an intraperitoneal injection of SVCVnc 28 days after vaccination Example 1

Susceptibility Testing of Goldfish and Koi

For development of a reliable challenge model to test the SVCV DNA vaccine, koi and goldfish were compared for susceptibility to SVCVnc by injection and immersion challenges. The majority of the goldfish (96%, n=160) exposed to SVCVnc survived both challenge experiments. One goldfish died in the $10^3$ PFU immersion challenge, but no mortalities occurred in the $10^4$ PFU and $10^5$ PFU treatments in the first experiment. Twenty percent (4/20) of the goldfish injected with $1\times10^6$ PFU died. In the second goldfish susceptibility experiment only one fish died (1/20) in the $10^5$ PFU immersion challenge. No other goldfish died (n 60) from the $10^3$ PFU/ml and $10^4$ PFU/ml immersion, or the $10^6$ PFU injection challenge groups. Negligible mortalities occurred in the mock challenged fish. Two mock injected goldfish fish died (10% CPM) in the first susceptibility experiment and no deaths occurred in mock-challenged fish from the second susceptibility experiment.

In the first preliminary experiment challenging koi to SVCVnc, 100% (6/6) of the koi died by injection of $1\times10^6$ PFU/fish and 67% (4/6) of koi died after immersion challenge with $1\times10^5$ PFU/ml. After the initial demonstration of koi susceptibility to SVCVnc in the preliminary experiment, the challenges were repeated with more koi in an expanded second experiment. One hundred percent (20/20) of the koi died after injection challenge and 75% (15/20) of the koi succumbed after immersion challenge to SVCVnc in the second koi susceptibility experiment. No mortalities occurred in the mock challenged koi from either experiment and no virus was detected in the tested survivors. The virus exposed koi, both from immersion and injection challenges, tested positive for virus with titers ranging from $3.8\times10^7$ to $5.0\times10^7$ PFU/g.

The results from the goldfish and koi susceptibility to SVCVnc are summarized in table 2. Overall, the majority (96%) of the goldfish exposed to SVCVnc survived both challenge experiments. In our susceptibility tests, goldfish did not succumb to SVCVnc infection, which indicated that these goldfish would not be good candidates for vaccine testing. In contrast, all koi died after the SVCVnc injection challenges and 71% of the koi succumbed after immersion challenges. Confirmation of this domestic koi stock's susceptibility to SVCVnc validated its usage as the positive control fish species in virus challenges and as a potential cyprinid host for SVCVnc vaccine development.

Example 2

Cold Stress Challenge in Koi

There was no significant difference in mortality between the two cold water stress treatments that the koi underwent prior to virus challenge (Table 3). The cumulative percent mortalities were identical between the two stress treatments for both immersion (75% CPM) and injection (100%) challenges. All the survivors tested and the one mortality from the mock challenged fish had no detectable virus (n=9). All the sampled dead fish and survivors from the virus-challenged koi tested positive for virus with high virus titers (n=19), nearly all (18/19) titers were above $1\times10^6$ pfu/g. The rapid cold stressor was adopted into the SVCV challenge model protocol since it was more efficient and produced the same mortalities as the slow acclimation cold stressor.

TABLE 2

Golfish (*Carassius auratus*) and koi
(*Cyprinus carpio* koi) susceptibility to SVCVnc

| Challenge method | Goldfish mortality[b] | | Koi mortality[b] | |
|---|---|---|---|---|
| and dose[a] | Exp 1 | Exp 2 | Exp 1 | Exp 2 |
| Immersion $1 \times 10^3$ pfu/ml | 1/20 | 0/20 | nt | nt |
| Immersion $1 \times 10^4$ pfu/ml | 0/20 | 0/20 | nt | nt |
| Immersion $1 \times 10^5$ pfu/ml | 1/20 | 1/20 | 4/6 | 15/20 |
| Mock Immersion | 0/20 | 0/20 | 0/6 | 0/20 |
| Injection $1 \times 10^6$ pfu/ml | 4/20 | 0/20 | 6/6 | 20/20 |
| Mock Injection | 4/20 | 0/20 | 0/6 | 0/20 |

[a] Fish were challenged with SVCVnc either by water bath immersion at the listed virus titer or intraperitoneally injected with $1 \times 106$ pfu. Mock challenged fish were exposed to culture media (MEM-10-SB).
[b] The mortality ratio listed is the number of dead fish over the total number of fish challenged in pooled data from duplicate tanks.
"nt" indicated not tested.

TABLE 3

Cold Water Stressor Comparison

| Challenge method | Two Weed Cold Water Stressor | | Rapid Cold Water Stressor | |
|---|---|---|---|---|
| and dose[a] | Mortality | MDD | Mortality | MDD |
| Mock injection | 5% | 0 | 0 | N/A |
| Mock immersion | 0 | N/A | 0 | N/A |
| Immersion $1 \times 10^5$ PFU/ml | 75% | 18 | 75% | 17 |
| Injection $1 \times 10^6$ PFU | 100% | 5 | 100% | 6 |

[a] Fish were challenged with SVCVnc either by water bath immersion or intraperitoneal injection. Mock challenged fish were exposed to culture media (MEM-10-SB).

Example 3

Vaccine Trials

The mock challenged fish experienced negligible mortalities ranging from 0-10% in all four trials (FIGS. 1*a*, 1*b*, 1*c*, and 1*d*). The small number of mock-challenged mortalities showed no clinical signs of disease and those fish screened for virus were negative. Mortalities in the mock exposed fish were most likely due to post-injection trauma immediately following the virus injection challenge.

In all four vaccine trials non-vaccinated fish exposed to virus suffered mortalities ranging from 70-100% (Table 4, FIGS. 1*a*, 1*b*, 1*c*, 1*d*). The virus challenged fish that were vaccinated with the pLuc construct had mortalities varying from 85-100% in the four trial experiments. Fish vaccinated with the SVCV DNA vaccine had low mortalities ranging from 10-50%. Differences in CPM among the pSGnc vaccine groups in the trials was expected for challenges with varying conditions, such as host age and challenge dose, as described in Table 1. The CPM, MDD, and RPS for each individual treatment group from the four trial experiments are summarized in table 4. In each trial the pSGnc vaccinated fish mortality was significantly lower than the mortalities that occurred in either the non-vaccinated or pLuc-vaccinated fish. Mortality curves from all four trials are displayed in FIGS. 1A, 1B, 1C, and 1D. The pSGnc construct conferred significant protection in fish 28 days after vaccination with RPS values ranging between 50 to 88%. The protection provided by the pSGnc DNA vaccine was significant at any virus exposure level ($p \leq 0.05$). In comparison with the NV fish groups, no protection (−21-0% RPS) was provided to the fish injected with the pLuc construct. The specific RPS values for the both pSGnc and pLuc groups from all the trial experiments are listed in Table 4.

Virus was detected in 98% (n=96) of the mortalities screened from the treatment groups exposed to virus from all four trials. The high virus concentrations ($7.9 \times 10^5$ to $1.8 \times 10^7$ PFU/g) corroborated that fish demise was most likely due to SVCV infection. Overall the prevalence and virus concentration in the survivors was lower than in the mortalities. Virus titers of the survivors testing positive ranged from $4.1 \times 10^3$ to $4.5 \times 10^5$ PFU/g. The survivors surveyed from each treatment group from every trial had at least one sample test positive for virus with the exception of the pSGnc vaccinated treatment groups. Survivors vaccinated with pSGnc from trial C and D had no detectable level of virus 30 days after virus exposure (n=23, Table 5).

TABLE 4

SVCV DNA Vaccine Trial Summary

| Treatment Group[a] | Trial A | | | Trial B | | | Trial C | | | Trial D | | |
|---|---|---|---|---|---|---|---|---|---|---|---|---|
| | CPM[b] | MDD[c] | RPS[d] | CPM[b] | MDD[c] | RPS[d] | CPM[b] | MDD[c] | RPS[d] | CPM[b] | MDD[c] | RPS[d] |
| NV | 100% | (7.3) | — | 100% | (5.8) | — | 80% | (7.3) | — | 70% | (8.9) | — |
| pLuc | 100% | (8.1) | 0% | 100% | (8.1) | 0% | 85% | (9.4) | −6.0% | 85% | (8.4) | −21% |
| pSGnc | 50%[e] | (8.9) | 50% | 30%[e] | (6.7) | 70% | 10%[e] | (11.0) | 88% | 35%[e] | (8.7) | 50% |

[a] Non-vaccinated (NV) fish, pLuciferase (pLuc) vaccinated fish, and fish vaccinated with the SVCV DNA vaccine (pSGnc).
[b] Values listed as cumulative percent mortality (CPM) average of duplicate treatment tanks.
[c] Mean day to death (MDD) listed in parentheses.
[d] Values listed as relative percent survival (RPS). RPS calculations based on the non-vaccinated group serving as the comparative control.
[e] Significance with p-values of <0.05 by Matel-Cox log-rank test (Systat 8.0).

TABLE 5

Virus titers in survivors after challenge in vaccine trials A-D

| Trial | Non-vaccinated[1] | pLuciferase[1] | pSGnc[1] |
|---|---|---|---|
| A | No survivors | No survivors | 1/6 (8.0 × 103) |
| B | No survivors | No survivors | 2/6 (4.1 × 103) |
| C | 3/3 (1.3 × 104) | 2/2 (4.5 × 105) | 0/10 (not detected) |
| D | 6/6 (6.5 × 103) | 3/3 (1.8 × 104) | 0/13 (not detected) |

[1] number of survivors positive for virus over the number of survivors tested for virus, followed in parentheses by the geometric mean (in pfu/g) of the positive survivor titers.

One of the primary tasks in the SVCV DNA vaccine research project was the development of a challenge model that could properly assess vaccine efficacy. The first fish tested as a possible cyprinid host was goldfish, since they were readily available, easy to rear, and reported to be susceptible to SVCV (Horvath et al. 2002, Carp and Pond Fish Culture, Blackwell Publishing, New York, N.Y. 192 p; Goodwin 2002, J. of Aquatic Animal Health 14, 161-164). However, the goldfish we tested had little to no susceptibility to the SVCVnc and would not have been a feasible candidate for pSGnc vaccination and testing. Koi, from a domestic US stock, were then tested since there is an established koi production and distribution industry in North America, and they were previously susceptible to at least three US strains of SVCV (Goodwin 2002, supra; Warg et al. 2007, Virus Genes 35, 87-95). Koi are highly popular fish among pond and aquarium enthusiasts, and their long life span endears them to their owners, similar to the feelings of attachment seen with other pet owners. Further showcase koi are extremely valuable, sales can exceed $100,000.00 for a single koi. For these reasons koi owners and farmers are more likely to vaccinate highly prized koi. We found a local koi distributor that annually breeds his own koi stock and provides a high standard of care in all fish husbandry at the farm. These specific pathogen-free koi have thrived in our wet laboratory and have reliably been susceptible to both immersion and injection challenges with SVCVnc in our aquatic BSL-3 laboratory.

The initial challenge model protocol included a two week cold stress period prior to virus challenge to mimic the temperatures that typically occur before a SVCV outbreak. Many researchers have a suggested a temperature stressor is needed (Ahne 1980, Veterinarmed. 30, 180-183; Ahne 1986, supra; Baudouy et al. 1980, In W. Ahne, ed. Fish Diseases. Third COPRAQ Session, Springer-Verlag, Berlin; Fijan et al. 1971, Veterinary Archives, 41, 125-138) to initiate successful SVCV infection in experimental models. Other researchers have suggested that a temperature stressor may not be the sole initiator of a successful SVCV in fish exposed to virus (Dixon 2005, Impacts, control and regulation of SVCV in wild and cultured fish in western Europe with a history of SVCV strains from China. 30$^{th}$ Eastern Fish Health Workshop, Spring Viremia of Carp Virus Continuing Education Course). It is possible that any environmental stressor (handling, pollutants, etc.) acting alone or in conjunction with water temperature fluctuations may facilitate SVCV outbreaks. Our experiments demonstrated no significant difference in mortalities between koi challenged after being held for two weeks at colder water temperatures versus koi challenged immediately after transferring from stock water temperatures of −18° C. to BSL-3 laboratory water temperatures ranging from 10-12° C. Our final challenge model included a rapid cold stressor on the day of virus challenge and utilized koi as the most susceptible fish host species to SVCVnc. These initial experiments also indicated that koi would be a suitable target species for vaccine development.

The pSGnc vaccinated fish challenged 28 days after vaccination had significantly lower mortalities compared to the pLuc vaccinated fish and non-vaccinated control fish. The RPS values of 50%-88% conveyed by the pSGnc vaccine in all four trials were comparable to or higher than RPS values reported from previously tested European SVCV DNA constructs, but lower than RPS values (>90%) typically reported for the novirhabdovirus (IHNV and VHSV) DNA vaccines (Kurath et al. 2007, supra). The absence of virus in the majority of the survivors vaccinated with pSGnc vaccine indicates that the fish had cleared the virus and completely recovered. The presence of virus in a few survivors from trials A and B may be attributed to the age of the fish used in those experiments and that the highest virus challenge dose was in trial B. The younger koi (~4 months old) used in the first trial studies (A & B) were at the fry life history stage and this may contribute to a slower clearance of the virus due to an underdeveloped immune system.

The four trial studies demonstrated that the SVCV DNA vaccine bestowed consistent and reproducible protection against a homologous North American SVCV isolate (SVCVnc) in immunized koi. Significant protection was present in the pSGnc-vaccinated fish tested under varying conditions (i.e., host age, virus dose, and season). The pSGnc construct is the most efficacious vaccine reported yet for any SVCV DNA construct. This is the first report of any SVCV DNA vaccine being tested successfully in a koi fish species. This efficacious SVCV DNA vaccine can be utilized as a prophylactic tool to stem the invasion of this exotic virus in North America.

What is claimed is:

1. A DNA vaccine comprising an expressible polynucleotide fragment which encodes an SCVCnc G polypeptide effective for protection from fatality due to Spring viremia of carp virus infection in a subject wherein said polynucleotide fragment consists of nucleotides 11-1538 of SEQ ID NO:1.

2. A DNA vaccine according to claim 1 wherein said polynucleotide is part of an expression vector.

3. The DNA vaccine of claim 2 wherein said subject is fish.

4. The DNA vaccine of claim 3 wherein said subject is fish susceptible to SVCV infection.

5. The DNA vaccine of claim 3 wherein said fish belong to the Cyprinidae family.

6. The DNA vaccine of claim 5 wherein said cyprinid is common carp *Cyprinus carpio carpio.*

7. The DNA vaccine of claim 5 wherein said cyprinid is koi.

8. The DNA vaccine of claim 7 wherein said koi is ornamental koi *Cyprinus carpio* koi.

9. The DNA vaccine of claim 5 wherein said cyprinid is selected from the group consisting of: goldfish, *carassius auratus*, crucian carp, *Carassius carassius*, silver carp, *Hypopthalmichthys molitirix*, bighead carp, *Aristichthys nobilis*, grass carp, *Ctenopharyngodon idella*, orfe, *Leucisucus idus*, and tench, *Tinca tinca*, roach, *Rutilus rutilius*, zebrafish, *Danio rerio*, and fathead minnow, *Pimephales promelas*.

10. The DNA vaccine of claim 3 wherein said fish belong to the families selected from the group consisting essentially of Poeciliidae, Esocidae, Centrarchidae, Siluridae, and Salmonidae.

11. A host cell transformed with the vector of claim 2.

12. The host cell of claim 11 wherein said host is a prokaryotic host.

13. The host cell of claim 12 wherein said host is *E. coli*.

14. The host cell of claim 11 wherein said host cell is eukaryotic.

15. A method for protecting a subject against fatality from infection with spring viremia of carp virus, comprising providing said subject a DNA vaccine comprising an expressible polynucleotide fragment which encodes an SCVCnc G polypeptide in an amount effective for protection from fatality due to Spring viremia of carp virus infection in said subject wherein said polynucleotide fragment consists of nucleotides 11-1538 of SEQ ID NO:1.

16. The method of claim 15 wherein said subject is fish susceptible to SVCV infection.

17. The method of claim 16 wherein said fish belong to the Cyprinidae family.

18. The method of claim 17 wherein said cyprinid is common carp *Cyprinus carpio carpio.*

19. The method of claim 18 wherein said cyprinid is koi.

20. The method of claim 18 wherein said koi is ornamental koi *Cyprinus carpio* koi.

21. The method of claim 17 wherein said cyprinid is selected from the group consisting of: goldfish, *carassius auratus*, crucian carp, *Carassius carassius*, silver carp, *Hypopthalmichthys molitirix*, bighead carp, *Aristichthys nobilis*, grass carp, *Ctenopharyngodon idella*, orfe, *Leucisucus idus*, and tench, *Tinca tinca*, roach, *Rutilus rutilius*, zebrafish, *Danio rerio*, and fathead minnow, *Pimephales promelas*.

22. The method of claim 16 wherein said fish belong to the families selected from the group consisting essentially of Poeciliidae, Esocidae, Centrarchidae, Siluridae, and Salmonidae.

* * * * *

SEQUENCE LISTING

```
<160> NUMBER OF SEQ ID NOS: 5

<210> SEQ ID NO 1
<211> LENGTH: 1598
<212> TYPE: DNA
<213> ORGANISM: Spring Viremia of Carp Virus (North Carolina)
<220> FEATURE:

<400> SEQUENCE: 1
aacagacatc atgtctatca tcagctacat cgcattcctt        40
ttgctaattg actccacatt tggaatcccc atatttgttc        80
catccgggca gaatatatca tggcaacctg taattcagcc       120
atttgattat caatgtccaa tacacggaaa tctacctaac       160
acaatgggat tgagtgccac caaattgaca ataaaatctc       200
catctgtctt cagtacagat aaagtttctg gatggatctg       240
ccatgcagct gaatggaaaa caacttgtga ttacagatgg       280
tacggacccc aatatataac ccacagtatt catccaatca       320
gtcctaccat agatgaatgc aagagaatca tttcaaggat       360
```

| | |
|---|---|
| tgcatcagga actgatgaag atctggggtt tccccctcaa | 400 |
| agttgcggat gggcatctgt cacaacagtg tcaaatacta | 440 |
| attacaaggt agtaccccat tctgttcatt tggagccgta | 480 |
| cggaggacac tggatcgatc atgaattcaa tggggggcgaa | 520 |
| tgcagagaaa aagtgtgtga atgaaaggg aaccactcta | 560 |
| tttggatcac agatgagacc gtgcagcatg aatgtgaaaa | 600 |
| gcacatagag gaagttgaag gaattatgta cgggaatgct | 640 |
| ccgagagggg atgcaatata tattaacaac tttattatag | 680 |
| ataaacatca tagagtatac agattcgggg ggtcttgtcg | 720 |
| aatgaaattc tgtaataaag atggtataaa attcacaaga | 760 |
| ggagactggg tagaaaaaac agctgaaaca ttgacgaata | 800 |
| tttatgcaaa tatacctgaa tgtgctgatg gaacgttggt | 840 |
| atctggtcac cgacctggat tagacttgat tgacacagtc | 880 |
| ttcaatttgg aaaatgtggt agaatatact ttgtgtgaag | 920 |
| ggactaaaag aaaaatcaat aaccaagaaa agttgacgtc | 960 |
| agtggatttg agttatttgg ccccaagaat tggagggttc | 1000 |
| ggatcagtat tcagagtgag aaacggaaca ttagagagag | 1040 |
| ggagcactac ttatatcaag atagaagtag agggacctat | 1080 |
| tgtcgactcg ttgaatggaa cagatccgag aaccaacgcc | 1120 |
| tcaagagtat tttgggacga ctgggagtta gatggcaata | 1160 |
| tatatcaggg cttttaatggt gtatataaag ggaaagatgg | 1200 |
| gaagatccat attcccttga atatgataga atcaggaatc | 1240 |
| atagatgatg aacttcaaca tgctttccaa gccgatatta | 1280 |
| tccctcatcc tcattatgac gacgatgaaa tccgagagga | 1320 |
| cgatatattc ttcgataata ctggagaaaa tggaaatccc | 1360 |
| gtggatgcag tggtagaatg ggtcagtggg tggggaacta | 1400 |
| gtctaaaatt ctttggcacg actctggtcg ccctgatttt | 1440 |
| gatctttctg ctcatcaggt gctgtgttgc ttgcacttat | 1480 |
| ttgatgaaga agagtaaacg gcctgcaaca gaatcacacg | 1520 |
| aaatgcggtc cttcgtttga gagatagcaa attttaagca | 1560 |
| aagaccaaga tattatctta ataggtgtat gaaaaaaa | 1598 |

<210> SEQ ID NO 2
<211> LENGTH: 25
<212> TYPE: DNA
<213> ORGANISM: Artificial sequence
<220> FEATURE:
<223> OTHER INFORMATION: SVCVnc G-gene forward primer

<400> SEQUENCE: 2

```
caccatgtct atcatcagct acatc                                      25
```

<210> SEQ ID NO 3
<211> LENGTH: 24
<212> TYPE: DNA
<213> ORGANISM: Artificial sequence -continued

```
<220> FEATURE:
<223> OTHER INFORMATION: SVCVnc G-gene reverse primer

<400> SEQUENCE: 3
ctaaacgaag gaccgcattt cgtg                                  24

<210> SEQ ID NO 4
<211> LENGTH: 20
<212> TYPE: DNA
<213> ORGANISM: Artificial sequence
<220> FEATURE:
<223> OTHER INFORMATION: internal SVCV G-gene primer 379+

<400> SEQUENCE: 4
tttccccctc aaagttgcgg                                       20

<210> SEQ ID NO 5
<211> LENGTH: 24
<212> TYPE: DNA
<213> ORGANISM: Artificial sequence
<220> FEATURE:
<223> OTHER INFORMATION: internal SVCV G-gene primers 978-/F1

<400> SEQUENCE: 5
tcttggagcc aaatagctca rrtc                                  24
```